United States Patent [19]
Noda

[11] Patent Number: 5,821,299
[45] Date of Patent: Oct. 13, 1998

[54] SOLVENT EXTRACTION OF POLYHYDROXY-ALKANOATES FROM BIOMASS FACILITATED BY THE USE OF MARGINAL NONSOLVENT

[75] Inventor: Isao Noda, Cincinnati, Ohio

[73] Assignee: The Proctor & Gamble Company, Cincinnati, Ohio

[21] Appl. No.: 802,969

[22] Filed: Feb. 21, 1997

Related U.S. Application Data

[63] Continuation of Ser. No. 601,317, Feb. 16, 1996, abandoned.

[51] Int. Cl.$^6$ .............................. C08K 5/16; C08G 63/06; C12P 7/62
[52] U.S. Cl. ........................... 524/725; 528/361; 528/491; 528/492; 528/493; 528/495; 528/499; 528/502; 528/503; 524/726; 524/729; 524/765; 524/767; 524/768; 524/770; 524/772; 524/800; 435/135; 435/141; 435/146; 435/271
[58] Field of Search ..................................... 528/361, 491, 528/492, 493, 495, 499, 502, 503; 435/135, 141, 146, 271; 524/725, 726, 729, 765, 767, 768, 770, 772, 800

[56] References Cited

U.S. PATENT DOCUMENTS

| | | | |
|---|---|---|---|
| 4,140,741 | 2/1979 | Lafferty et al. | 264/184 |
| 4,310,684 | 1/1982 | Vanlautem et al. | 560/185 |
| 4,324,907 | 4/1982 | Senior et al. | 560/185 |
| 4,358,583 | 11/1982 | Walke et al. | 528/491 |
| 4,391,766 | 7/1983 | Barham et al. | 264/210.1 |
| 4,562,245 | 12/1985 | Stageman | 528/361 |
| 4,705,604 | 11/1987 | Vanlautem et al. | 203/67 |
| 4,910,145 | 3/1990 | Holmes et al. | 435/259 |
| 4,968,611 | 11/1990 | Traussnig et al. | 435/135 |
| 5,213,976 | 5/1993 | Blaubut | 435/135 |

FOREIGN PATENT DOCUMENTS

| | | |
|---|---|---|
| 0 036 699 A1 | 9/1981 | European Pat. Off. . |
| 0 046 335 A2 | 2/1982 | European Pat. Off. . |
| 0 452 111 A2 | 10/1991 | European Pat. Off. . |
| 229 428 A1 | 11/1985 | Germany . |
| 239 609 A1 | 10/1986 | Germany . |
| 294 280 A5 | 9/1991 | Germany . |
| 42 15 860 A1 | 11/1993 | Germany . |
| 62-205787 | 9/1987 | Japan . |
| 63-198991 | 8/1988 | Japan . |
| 6-181784 | 7/1994 | Japan . |

(List continued on next page.)

OTHER PUBLICATIONS

Bleich, J., Müller, B.W., and Waβmus, W., (Aug. 15, 1993) "Aerosol Solvent Extraction System–A New Microparticle Production Technique", International Journal of Pharmaceutics 97(1–3) 111–117.

Ito, H. Marchessault, R. H., and St. John Manley, R., (1991) "Uniaxial Deformation of Poly(β–hydroxybutyrate– co–hydroxyvalerate) Gel Films", Polymer Communications 32(6) 164–167.

Mitomo, H., Morishita, N. and Doi, Y., (Jun. 1995) "Structural Changes of Poly(3–hydroxybutyrate–co– 3–hydroxy–valerate) Fractionated with Acetone–water Solution", Polymer 36(13) 2573–2578.

*Primary Examiner*—Samuel A. Acquah
*Attorney, Agent, or Firm*—Brahm J. Corstanje; Bart S. Hersko; David L. Suter

[57] ABSTRACT

The present invention relates to a process for separating polyhydroxyalkanoate (PHA) from a biomass comprising the PHA, the process comprising: a) treating the biomass with a PHA solvent and a marginal nonsolvent for PHA; b) removing any insoluble biomass, thereby leaving behind a solution of PHA and marginal nonsolvent for PHA; and c) removing the PHA solvent from the solution, thereby resulting in a suspension of precipitated PHA in the marginal nonsolvent for PHA. Optionally, the process further comprises removing the marginal nonsolvent for PHA, thereby leaving behind the PHA. The present invention further relates to the suspension and the PHA produced by the process.

35 Claims, 1 Drawing Sheet

FOREIGN PATENT DOCUMENTS

| | | |
|---|---|---|
| 7-031487 | 2/1995 | Japan . |
| 7-031489 | 2/1995 | Japan . |
| 7-79788 | 3/1995 | Japan . |
| 7-135985 | 5/1995 | Japan . |
| RO-79661 | 7/1982 | Romania . |
| 2 089 823 | 6/1982 | United Kingdom . |
| 2 120 671 | 12/1983 | United Kingdom . |
| 92/18553 | 10/1992 | WIPO . |
| 93/02187 | 2/1993 | WIPO . |
| 93/11656 | 6/1993 | WIPO . |
| 96/06179 | 2/1996 | WIPO . |

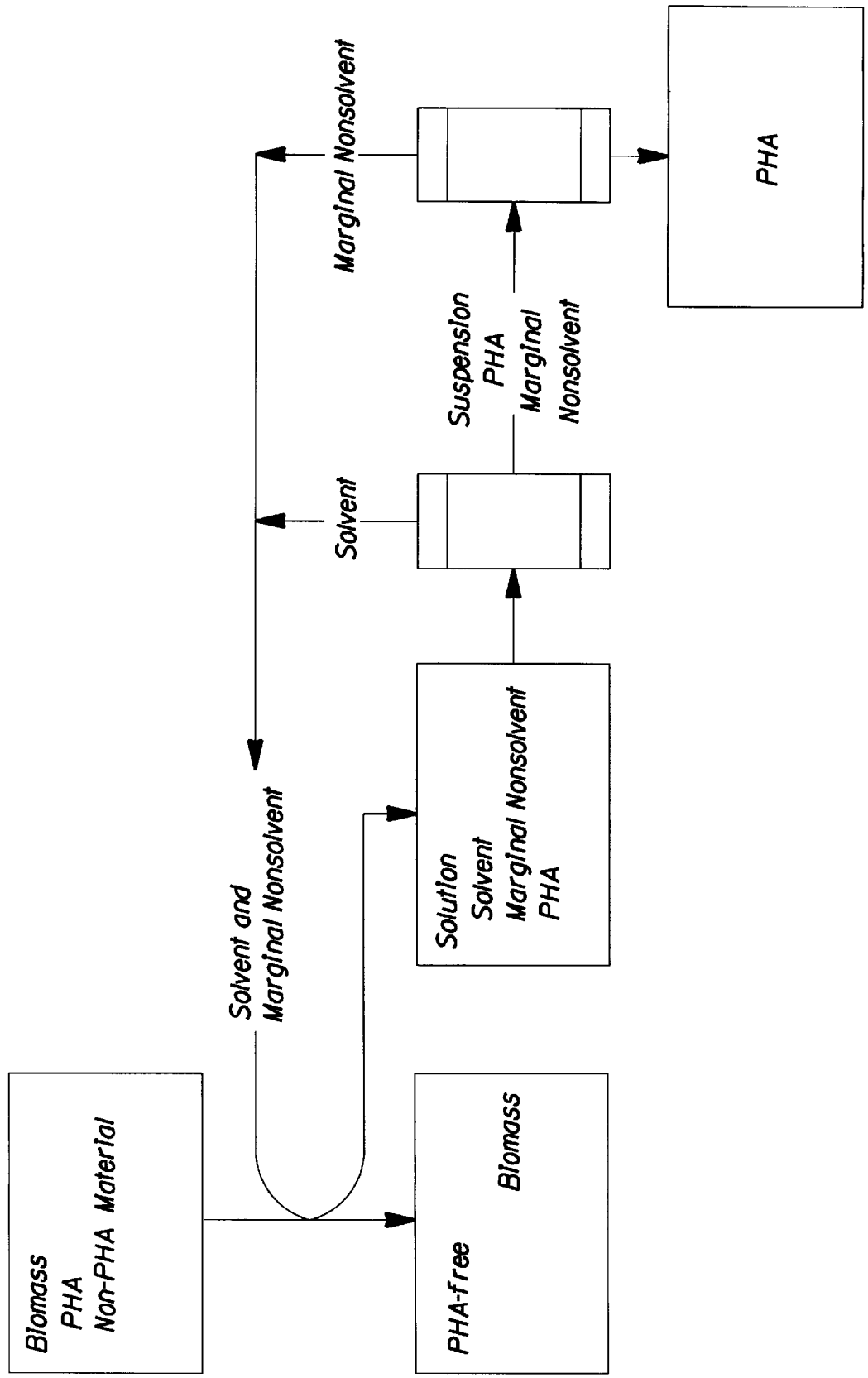

form. Also described for use are other halogenated hydrocarbon solvents such as dichloromethane, dichlorethane and chloropropane (see, e.g., U.S. Pat. No. 4,562,245, Stageman, issued Dec. 31, 1985; U.S. Pat. No. 4,324,907, Senior, Wright and Alderson, issued Apr. 13, 1982; U.S. Pat. No. 4,310,684, Vanlautem and Gilain, issued Jan. 12, 1982; U.S. Pat. No. 4,705,604, Vanlautem and Gilain, issued Nov. 10, 1987; European Patent Application 036 699, Holmes and Wright, published Sep. 3, 1981; and German Patent Application 239 609, Schmidt, Schmiechen, Rehm and Trennert, published Jan. 10, 1986). In the process of stripping the solvent, the concentrated PHA solution often forms a very high viscosity fluid or sometimes even a gel; which can be extremely difficult to process. Furthermore, such solvents are potentially harmful to health and environment if not fully removed from the PHA. Consequently, the use of a large amount of such solvents resulting in the formation of highly viscous solutions or gels, especially near the harvesting site, would be undesirable.

SOLVENT EXTRACTION OF POLYHYDROXY-ALKANOATES FROM BIOMASS FACILITATED BY THE USE OF MARGINAL NONSOLVENT

This is a nonprovisional application of provisional application Ser. No. 60/002,567, filed Aug. 21, 1995, now abandoned.

This is a continuation of application Ser. No. 08/601,317, filed on Feb. 1, 1996

FIELD

The present invention relates to methods of extracting specific components from other biomass components. More specifically, the present invention relates to the extraction of a polyhydroxyalkanoate from a biological system, such as a plant or bacteria, by performing the extraction with a solvent; the extraction process being facilitated by the use of a marginal nonsolvent for PHA.

BACKGROUND

Commodity polymers are typically produced from petrochemical sources by well-known synthetic means. However, recent advances in technology have resulted in the promise of new sources of commodity polymers. Particularly promising is the production of plastic resins using living organisms ("bioplastic"), including genetically manipulated bacteria and crop plants, which are designed to produce polymers such as polyhydroxyalkanoate (PHA); a number of bacteria which naturally produce PHA are also promising sources of PHA. (See for example, Poirier, Y., D. E. Dennis, K. Klomparens and C. Somerville, "Polyhydroxybutyrate, a biodegradable thermoplastic, produced in transgenic plants", SCIENCE, Vol. 256, pp. 520–523 (1992); World Patent Application Publication No. 95/05472, published Feb. 23, 1995; and World Patent Application Publication No. 93/02187, published Feb. 4, 1993; NOVEL BIODEGRADABLE MICROBIAL POLYMERS, E. A. Dawes, ed., NATO ASI Series, Series E: Applied Sciences—Vol. 186, Kluwer Academic Publishers (1990)). In a large scale production, for example agricultural production, the harvesting and purifying of such bioplastic from the biomass debris is a critical step for determining the practical feasibility of such technology.

The separation of polymeric lipids such as PHA from a large-scale biological source, such as an agricultural crop, is not a trivial task. The conventional separation methods used extensively in the extraction of low molecular weight lipids are not practical to employ in a resin isolation process. For example, a simple mechanical press is impractical because, unlike separating vegetable oils from oilseeds, solid plastics cannot be squeezed out of crops by mechanical pressing.

Separation of PHA by sedimentational methods should be, in principle, possible. However, simple gravitational (1-G force) settling in a liquid marginal nonsolvent for PHA is, in fact, quite impractical. The rate of settling is extremely slow. In addition, such slow settling is easily disrupted by the Brownian motion of the fine PHA particles induced by the thermal fluctuation of the suspending fluid molecules surrounding the particles. Furthermore, the extended period of time required to settle very fine PHA particles introduces the problem of bacterial contamination and subsequent biodegradation of the particle suspension.

Known solvent extraction methods are also limited for a large-scale separation of PHA from a biomass. A commonly used solvent for the extraction of PHA from bacteria is chloroform.

Based on the foregoing, there is a need for a simple and economical process for recovering bioplastics from a large-scale biological source. Such a process would preferably be easily adaptable for use in standard fermentation-based production for bacterial PHA. Such a process would also preferably be easily adaptable as an integral part of the agricultural production of related commodities, e.g., oil and meal in the case of oilseeds.

It is therefore an object of the present invention to provide a process for recovering bioplastics from a biomass.

These and other objects of the present invention will become evident to those skilled in the art from a reading of the present disclosure with the appended claims.

SUMMARY

The present invention relates to a process for separating polyhydroxyalkanoate (PHA) from a biomass comprising the PHA, the process comprising: a) treating the biomass with a PHA solvent and a marginal nonsolvent for PHA; b) removing any insoluble biomass, thereby leaving behind a solution of PHA and marginal nonsolvent for PHA; and c) removing the PHA solvent from the solution, thereby resulting in a suspension of precipitated PHA in the marginal nonsolvent for PHA. Optionally, the process further comprises removing the marginal nonsolvent for PHA, thereby leaving behind the PHA. The present invention further relates to the suspension and the PHA produced by the process.

Such a process satisfies the need for a relatively simple and economical process for recovering bioplastics from a large-scale biological source.

BRIEF DESCRIPTION OF THE DRAWINGS

FIG. 1 sets forth a schematic of an embodiment of the invention wherein a marginal nonsolvent for PHA from an outside source is added (and later removed) to facilitate extraction of the PHA.

DETAILED DESCRIPTION

The following is a list of definitions for terms used herein.

"Alkane" means a saturated hydrocarbon having the general formula $C_nH_{2n+2}$; preferably n is from about 3 to about 20; more preferably n is from about 6 to about 16.

"Alkenyl" means a carbon-containing chain, preferably from about $C_2$ to about $C_{24}$, more preferably from about $C_2$ to about $C_{19}$; which may be straight, branched or cyclic, preferably straight or branched, more preferably straight; substituted (mono- or poly-) or unsubstituted; and monounsaturated (i.e., one double or triple bond in the chain), or polyunsaturated (i.e., two or more double bonds in the chain, two or more triple bonds in the chain, or one or more double and one or more triple bonds in the chain), preferably monounsaturated.

"Alkyl" means a carbon-containing chain, preferably from about $C_1$ to about $C_{24}$, more preferably from about $C_1$ to about $C_1$; which may be straight, branched or cyclic, preferably straight or branched, more preferably straight; substituted (mono- or poly-) or unsubstituted; and saturated.

"Comprising" means that other steps and other ingredients which do not affect the end result can be added. This term encompasses the terms "consisting of" and "consisting essentially of".

"Extracting polyhydroxyalkanoate from a biomass", in addition to referring to the extraction of the particular PHA produced by a biomass which produces a single PHA, also refers to the extraction of one or more types of PHA when the biomass produces more than one type of PHA.

"Polyhydroxyalkanoate" and "PHA" mean a polymer comprising the following repeating unit:

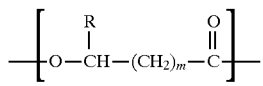

wherein R is preferably H, alkyl or alkenyl; and m is from about 1 to about 4.

The terms polyhydroxyalkanoate and PHA include polymers containing one or more different repeating units.

PHAs extractable by the process of the present invention preferably have a melt temperature ("Tm") of about 80° C. or higher. Preferably, such PHAs comprise at least two randomly repeating monomer units, wherein the first randomly repeating monomer unit has the structure

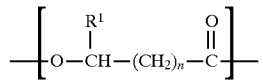

wherein $R^1$ is H, or $C_1$ to $C_2$ alkyl; and n is 1 or 2; the second randomly repeating monomer unit has the structure

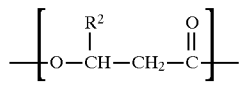

wherein $R^2$ is $C_3$ to $C_{19}$ alkyl or $C_3$ to $C_{19}$ alkenyl; and wherein at least 50% of the randomly repeating monomer units have the structure of the first randomly repeating monomer unit. More preferably, examples of high crystallinity PHAs extractable by the present process include those disclosed in U.S. patent application Ser. No. 08/465,046, Noda, filed Jun. 6, 1995; U.S. patent application Ser. No. 08/422,008, Noda, filed Apr. 13, 1995; U.S. patent application Ser. No. 08/422,009, Noda, filed Jun. 5, 1995; U.S. patent application Ser. No. 08/467,373, Noda, filed Jun. 6, 1995; U.S. patent application Ser. No. 08/188,271, Noda, filed Jan. 28, 1994; U.S. patent application Ser. No. 08/469,969, Noda, filed Jun. 6, 1995; U.S. patent application Ser. No. 08/472,353, Noda, filed Jun. 7, 1995; U.S. patent application Ser. No. 08/469,269, Noda, filed Jun. 6, 1995; and U.S. Pat. No. 5,292,860, Shiotani and Kobayashi, issued Mar. 8, 1994.

"Solvent" means a substance capable of dissolving another substance (solute) to form a uniformly dispersed mixture (solution) at the molecular or ionic size level.

"Nonsolvent" means a substance which is incapable of appreciably dissolving another substance.

"Marginal nonsolvent" means a substance which is a nonsolvent by itself, however, when mixed with a solvent, becomes capable of dissolving solute.

"Precipitant" means a substance which is capable of inducing the precipitation of another substance and/or weakening the solvating power of a solvent. While a precipitant is also considered a nonsolvent, however, a nonsolvent is not always a precipitant. For example, methanol and hexane are PHA precipitants and PHA nonsolvents; whereas oil is a PHA nonsolvent, but not a very effective PHA precipitant (though at extremely high concentrations, oil will cause PHA to precipitate out of solution).

All percentages are by mole % of total composition unless specifically stated otherwise.

All ratios are weight ratios unless specifically stated otherwise.

The present invention, in its product and process aspects, is described in detail as follows.

Biomass

Sources from which PHA is extracted via the process of the present invention include single-cell organisms such as bacteria or fungi and higher organisms such as plants (herein collectively referred to as "biomass"). While such biomass could be wild-type organisms, they are preferably genetically manipulated species specifically designed for the production of a specific PHA of interest to the grower. Such genetically manipulated organisms are produced by incorporating the genetic information necessary to produce one or more types of PHA. Typically, such genetic information is derived from bacteria which naturally produce PHA.

Plants useful in the present invention include any genetically engineered plant designed to produce PHA. Preferred plants include agricultural crops such as cereal grains, oilseeds and tuber plants; more preferably, avocado, barley, beets, broad bean, buckwheat, carrot, coconut, copra, corn (maize), cottonseed, gourd, lentils, lima bean, millet, mung bean, oat, oilpalm, peas, peanut, potato, pumpkin, rapeseed (e.g., canola), rice, sorghum, soybean, sugarbeet, sugar cane, sunflower, sweetpotato, tobacco, wheat, and yam. Such genetically altered fruit-bearing plants useful in the process of the present invention include, but are not limited to, apple, apricot, banana, cantaloupe, cherries, grapes, kumquat, lemon, lime, orange, papaya, peaches, pear, pineapple, tangerines, tomato, and watermelon. Preferably the plants are genetically engineered to produce PHA pursuant to the methods disclosed in Poirier, Y., D. E. Dennis, K. Klomparens and C. Somerville, "Polyhydroxybutyrate, a biodegradable thermoplastic, produced in transgenic plants", SCIENCE, Vol. 256, pp. 520–523 (1992); World Patent Application Publication No. 95/05472, Somerville, et al., published Feb. 23, 1995; and World Patent Application Publication No. 93/02187, Somerville, et al., published Feb. 4, 1993. Particularly preferred plants are soybean, potato, corn and coconut plants genetically engineered to produce PHA; more preferably, soybean.

Bacteria useful in the present invention include any genetically engineered bacteria designed to produce PHA, as well as bacteria which naturally produce PHA. Examples of such bacteria include those disclosed in NOVEL BIODEGRADABLE MICROBIAL POLYMERS, E. A. Dawes, ed., NATO ASI Series, Series E: Applied Sciences—Vol. 186, Kluwer Academic Publishers (1990); U.S. Pat. No. 5,292,860, Shiotani and Kobayashi, issued Mar. 8, 1994; U.S. Pat. No. 5,250,430, Peoples and Sinskey, issued Oct. 5, 1993;

U.S. Pat. No. 5,245,023, Peoples and Sinskey, issued Sep. 14, 1993; U.S. Pat. No. 5,229,279, Peoples and Sinskey, issued Jul. 20, 1993.

Solvent Extraction Facilitated by the Addition of a Marginal nonsolvent for PHA The present invention relates to a process for separating polyhydroxyalkanoate (PHA) from a biomass comprising the PHA, the process comprising: a) treating the biomass with a PHA solvent and a marginal nonsolvent for PHA; b) removing any insoluble biomass, thereby leaving behind a solution of PHA and marginal nonsolvent; and c) removing the PHA solvent from the solution, thereby resulting in a suspension of precipitated PHA in the marginal nonsolvent for PHA. Optionally, the process further comprises removing the marginal nonsolvent for PHA, thereby leaving behind the PHA. The solution formed at step b) is made up of the marginal nonsolvent for PHA dissolved or dispersed in the PHA solvent.

The present invention further relates to the suspension and the PHA produced by the process.

Preferably the PHA solvent is acetone, acetonitrile, benzene, butyl acetate, butyl propionate, β-butyrolactone, γ-butyrolactone, liquified carbon dioxide, chloroform, 1,2-dichloroethane, diethyl carbonate, diethylformamide, dimethyl carbonate, dimethyl succinate, dimethyl sulfoxide, demethylformamide, 1,4-dioxane, ethyl acetate, ethylene glycol diacetate, methyl acetate, methyl ethyl ketone, 1,1,2,2-tetrachloroethane, tetrahydrofuran, 1,1,2-trichloroethane, 1,2,3-trichloropropane, toluene, xylene, or mixtures thereof.

More preferably, the PHA solvent is acetone, acetonitrile γ-butyrolactone, 1,4-dioxane, methyl acetate, toluene, methyl ethyl ketone, ethyl acetate or mixtures thereof.

In a more environmentally benign process, the PHA solvent preferably is acetone, butyl acetate, ethyl acetate, methyl acetate, or mixtures thereof; more preferably acetone or ethyl acetate; more preferably still, acetone.

Preferably the PHA solvent is employed in the process at an elevated temperature, as the rate of dissolution of PHA in the PHA solvent at elevated temperatures has been found to be substantially faster. While extraction of the PHA may be conducted between about 20° C. and the melt temperature of the PHA; more preferably between about 20° C. and about 80° C.; more preferably between about 45° C. and the boiling point of the PHA solvent; more preferably still, from about 50° C. to about 60° C.

Preferably the solid mass containing the PHA is stirred during extraction with the PHA solvent, as this also accelerates the rate of dissolution of the PHA.

The removal of the PHA solvent from a solution containing PHA results in the eventual precipitation of PHA as crystalline solids. In the process of stripping the solvent, however, the concentrated PHA solution often forms a very high viscosity fluid or sometimes even a gel; which can be extremely difficult to process. If the solution contains a marginal nonsolvent for PHA which is relatively nonvolatile, the PHA will precipitate upon the removal of the PHA solvent and form a suspension in the marginal nonsolvent for PHA.

The present invention is exemplified in schematic form in FIG. 1. This process enables one to obtain the advantages of a marginal nonsolvent for PHA (e.g., oil) for the precipitating PHA, even when the marginal nonsolvent for PHA is not present in the starting biomass (e.g., non-oilseed biomass, or bacteria). The marginal nonsolvent for PHA acts as a process aid by impeding the build up of excessive viscosity or gelation during the stripping of PHA solvent from the biomass.

The marginal nonsolvent for PHA must not significantly interfere with the solvating power of the PHA solvent, as it will be mixed with the PHA solvent during the extraction process. By itself, the marginal nonsolvent for PHA should not appreciably dissolve PHA, as dissolution of the PHA would preclude suspension of the PHA as discrete particles. Preferably, the marginal nonsolvent for PHA is less volatile (i.e., has a lower boiling point) than the PHA solvent. Such a lower volatility will provide for easier and cleaner separation of the PHA solvent. Preferably, the boiling point of the marginal nonsolvent for PHA is at least about 5° C. higher than the PHA solvent; more preferably at least about 10° C. higher; more preferably at least about 20° C. higher; more preferably still, at least about 40° C. higher.

Preferably the marginal nonsolvent for PHA is a $C_3$—$C_{20}$ alcohol, $C_1$—$C_{20}$ alkane, fat, neutral lipid, oil, water, or mixtures thereof.

Preferred alkanes include decane, dodecane, hexadecane, and octadecane.

Preferred alcohols include hexanol, lauryl alcohol, octanol, oleyl alcohol, and stearyl alcohol.

Preferred fats include tallow, grease, and wax.

Preferred neutral lipids include mono-, di- and trilycerides of oleic acid, inoleic acid and linelenic acid; lauric acid; stearic acid; and palmitic acid.

Preferred oils include mineral oils and vegetable oils (e.g., soybean, canola, and the like).

The previously described embodiments of the present invention have many surprising advantages, including avoidance of forming a high viscosity fluid or gel of PHA, which otherwise can be extremely difficult to process. This is achieved by conducting the extraction of PHA in the presence of the marginal nonsolvent for PHA. The marginal nonsolvent for PHA may initially serves as a miscible co-solvent to promote the extraction of PHA. However, upon removal of the relatively volatile PHA solvent, the marginal nonsolvent for PHA will become an effective suspending medium for the precipitating PHA (as discrete particles) due to its limited PHA-solvating power. Compared to a concentrated solution, a suspension of polymer solid in a fluid nonsolvent typically has much lower apparent viscosity and thus possesses superior processability. The elimination of the serious problem of gelation often encountered during the stripping of solvent from a concentrated polymer solution is an unexpected and significant advantage of the invention.

Another surprising advantage of the present process is its ability to produce suspensions of PHA which can be used, for example, as coatings, binders, additives for paints, food, adhesives; as well as carriers for dyes, pigments, bioactives and perfumes.

An additional surprising advantage of is found in certain embodiments of the present invention which have the ability to extract crystallizable high melt temperature (about 80° C. or higher) PHA without using solvent containing halogens. The relatively environmentally benign PHA solvents used in such embodiments of the invention such as acetone and ethyl acetate, are inexpensive, safe and readily available, even from renewable sources. Such PHA solvents are also considered far less damaging to the environment, especially the ozone layer of the earth, compared to halogen containing compounds typically used for the extraction of PHAs from bacteria.

Additionally, the discovery of the utility of certain substances used herein which were heretofore unknown to be useful as solvents of crystalline polymers having relatively high melt temperatures is not a trivial task. Unlike most low molecular weight compounds and noncrystallizable amorphous polymers, the solubility of crystalline polymers cannot be predicted from the commonly used simple criteria, such as the similarity of chemical architecture or matching of refractive indices, dielectric constants or solubility parameters. A good example for the inability to predict the solubility of crystalline polymers is the well-known insolubility of linear polyethylene in hexane, where both compounds are made of the identical hydrocarbon repeat units. Similarly, crystalline aliphatic polyesters like isotactic poly(3-hydroxybutyrate) and poly(3-hydroxybutyrate-co-3-hydroxyvalerate) are not appreciably soluble in ethyl acetate or acetone, even though the chemical structures of these compounds may suggest certain molecular affinity. Thus, the fortuitous discovery that crystalline PHA containing a small amount of medium size branches can be readily dissolved in such solvents is indeed surprising.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE 1

Extraction of PHA from *Aeromonas cavie*

The following procedure improves upon the method for isolating PHA from *Aeromonas cavie* as set forth in U.S. Pat. No. 5,292,860, Shiotani and Kobayashi, issued Mar. 8, 1994. A fermentation batch of *Aeromonas cavie* is centrifuged, washed with water and methanol, and vacuum dried to yield 120 g of dry cell. The dry cell biomass is then placed in a closed container with a mixture of 800 mL of chloroform and 200 mL of dodecane for 5hrs at 50° C. The insoluble solid biomass is then removed by using a wire-mesh filter. Chloroform is then removed from the solution mixture under reduced pressure at 50° C. and collected with a water-chilled condenser for further use. The removal of chloroform results in the formation of a suspension comprising solid flakes of poly(3-hydroxybutyrate-co-3-hydroxyhexanoate) dispersed in the remaining dodecane. The flakes are separated from dodecane using a fine-mesh filter, rapidly washed with the chilled chloroform, and dried to yield 7 g of poly(3-hydroxybutyrate-co-3-hydroxyhexanoate).

EXAMPLE 2

Extraction of PHA from *Alcaligenes eutrophus*

The following procedure improves upon the method for isolating PHA from *Alcaligenes eutrophus* as set forth in U.S. Pat. No. 4,562,245, Stageman, issued Dec. 31, 1985. Spray dried *Alcaligenes eutrophus* cells containing poly(3-hydoxybutyrate-co-3-hydroxyvalerate) are refluxed in methanol for 15 minutes at atmospheric pressure to remove soluble lipids. The cells are dried on a tray at 30° C. in an forced air tunnel. 10 g of dried cells are refluxed with a mixture of 250 mL of chloroform and 50 mL of hexadecane at atmospheric pressure for 30 minutes to extract poly(3-hydoxybutyrate-co-3-hydroxyvalerate). The resultant slurries are filtered to remove cell residues. The chloroform is then removed from the extraction solution under a reduced pressure, thereby leaving behind a suspension of hard solid flakes of poly(3-hydoxybutyrate-co-3-hydroxyvalerate) dispersed in hexadecane. The flakes are then collected by draining hexadecane to yield 6.2 g of poly(3-hydoxybutyrate-co-3-hydroxyvalerate).

EXAMPLE 3

Extraction of PHA from *Pseudomonas cepacia*

The following procedure improves upon the method for isolating PHA from *Pseudomonas cepacia* as set forth in World Patent Application 92/18553, published Oct. 29, 1992. *Psedomonas cepacia* cells containing copolymer consisting mainly of 3-hydoxyoctanoate are centrifuged, decanted, and resuspended in water four times, and then freeze dried. 10 g of dried cells are refluxed with a mixture of 250 mL of acetone and 50 mL of 1-hexanol at atmospheric pressure for 20 minutes to extract the 3-hydroxyoctanoate copolymer. The resultant slurries are filtered to remove cell residues. The acetone is then removed from the extraction solution under a reduced pressure, thereby leaving behind a suspension of soft solid particles of 3-hydroxyoctanoate copolymer dispersed in 1-hexanol. The flakes are then collected by draining hexadecane to yield 4.8 g of copolymer.

EXAMPLE 4

Extraction of PHA from Potato 60 g of transgenic potato (produced, e.g., by the process set forth in World Patent Application Publication No. 95/05472, Somerville, et al., published Feb. 23, 1995; or World Patent Application Publication No. 93/02187, Somerville, et al., published Feb. 4, 1993 sample comprising poly(3-hydroxybutyrate-co-3-hydroxyheptanoate) containing 7.5% 3-hydroxyheptanoate repeat units is placed in a closed container charged with 600 mL of acetone and 150 mL vegetable oil and stirred for 3 hrs at 55° C. The acetone solution containing the oil and PHA is then drained from the potato using a wire-mesh filter. The extraction solution containing vegetable oil, poly(3-hydroxybutyrate-co-3-hydroxyheptanoate) and acetone is placed in a steam-heated kettle to boil off the volatile acetone, which is collected by a water-chilled condenser. After the removal of the acetone, solid flakes of poly(3-hydroxybutyrate-co-3-hydroxyheptanoate) appear in the remaining oil which are drained by using a fine mesh filter to yield 7 g of pure vegetable oil. The polymer flakes are washed with cold acetone, previously collected by the condenser, to remove the residual entrained oil and then dried to yield 6 g of crystalline solid of poly(3-hydroxybutyrate-co-3-hydroxyheptanoate). The acetone used for the washing, is combined with the vegetable oil, and then used for further extraction of poly(3-hydroxybutyrate-co-3-hydroxyheptanoate).

All publications, issued patents and patent applications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A process for separating polyhydroxyalkanoate from a biomass comprising the polyhydroxyalkanoate, the process comprising:

a) treating the biomass with a PHA solvent and a marginal nonsolvent for PHA;
b) removing any insoluble biomass, thereby leaving behind a solution of polyhydroxyalkanoate and marginal nonsolvent for PHA; and
c) removing the PHA solvent from the solution, thereby resulting in a suspension of precipitated polyhydroxyalkanoate in the marginal nonsolvent for PHA;

wherein said PHA solvent is acetone, benzene, butyl acetate, butyl propionate, liquified carbon dioxide, chloroform, 1,2-dichloroethane, diethyl carbonate, diethylformamide, dimethyl carbonate, dimethyl sulfoxide, dimethylformamide, ethyl acetate, methyl acetate, methyl ethyl ketone, 1,1,2,2-tetrachloroethane, 1,1,2-trichloroethane, 1,2,3-trichloropropane, toluene, xylene, or mixtures thereof.

2. The process of claim 1, wherein the PHA solvent is acetone, liquified carbon dioxide, chloroform, 1,2-dichloroethane, ethyl acetate, 1,1,2,2-tetrachloroethane, 1,1,2-trichloroethane, 1,2,3-trichloropropane, or mixtures thereof.

3. The process of claim 2, wherein the PHA solvent is acetone or ethyl acetate.

4. The process of claim 3, wherein the biomass is bacteria.

5. The process of claim 4, wherein the biomass is plant material.

6. The process of claim 2, wherein the PHA solvent is chloroform or 1,2-dichloroethane.

7. The process of claim 6, wherein the biomass is bacteria.

8. The process of claim 6, wherein the biomass is plant material.

9. The process of claim 1, wherein the polyhydroxyalkanoate comprises the following repeating unit:

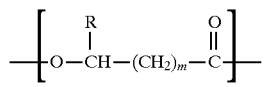

wherein R is H, alkyl or alkenyl; and m is from about 1 to about 4.

10. The process of claim 9, wherein the polyhydroxyalkanoate comprises at least two randomly repeating monomer units, wherein the first randomly repeating monomer unit has the structure

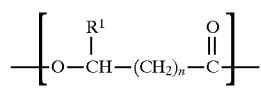

wherein $R^1$ is H or $C_1$ to $C_2$ alkyl, and n is 1 or 2; the second randomly repeating monomer unit has the structure

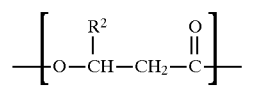

wherein $R^2$ is $C_3$ to $C_{19}$ alkyl or $C_3$ to $C_{19}$ alkenyl; and wherein at least 50% of the randomly repeating monomer units have the structure of the first randomly repeating monomer uritt.

11. The process of claim 1, wherein the process further comprises removing the marginal nonsolvent for PHA, thereby leaving behind the polyhydroxyalkanoate.

12. The process of claim 11, wherein the PHA solvent is acetone, methyl acetate, toluene, methyl ethyl ketone, ethyl acetate or mixtures thereof.

13. The process of claim 12, wherein the PHA solvent is acetone or ethyl acetate.

14. The process of claim 13, wherein the biomass is bacteria.

15. The process of claim 13, wherein the biomass is plant material.

16. The process of claim 12, wherein the PHA solvent is chloroform or 1,2-dichloroethane.

17. The process of claim 16, wherein the biomass is bacteria.

18. The process of claim 16, wherein the biomass is plant material.

19. The process of claim 16, wherein the polyhydroxyalkanoate comprises the following repeating unit:

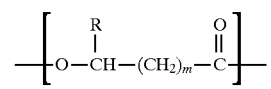

wherein R is preferably H, alkyl or alkenyl; and m is from about 1 to about 4.

20. The process of claim 19, wherein the polyhydroxyalkanoate comprises at least two randomly repeating monomer units, wherein the first randomly repeating monomer unit has the structure

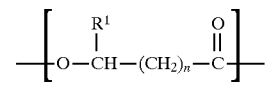

wherein $R^1$ is H or $C_1$ to $C_2$ alkyl, and n is 1 or 2; the second randomly repeating monomer unit has the structure

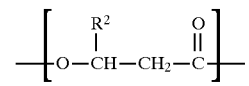

wherein $R^2$ is $C_3$ to $C_{19}$ alkyl or $C_3$ to $C_{19}$ alkenyl; and wherein at least 50% of the randomly repeating monomer units have the structure of the first randomly repeating monomer unit.

21. The suspension of claim 1.
22. The suspension of claim 4.
23. The suspension of claim 5.
24. The suspension of claim 7.
25. The suspension of claim 8.
26. The suspension of claim 10.
27. The polyhydroxyalkanoate of claim 11.
28. The polyhydroxyalkanoate of claim 14.
29. The polyhydroxyalkanoate of claim 15.
30. The polyhydroxyalkanoate of claim 17.
31. The polyhydroxyalkanoate of claim 18.
32. The polyhydroxyalkanoate of claim 19.
33. The polyhydroxyalkanoate of claim 20.
34. The process of claim 1, wherein the marginal nonsolvent for PHA is a $C_3$—$C_{20}$ alcohol, $C_1$—$C_{20}$ alkane, fat, neutral lipid, oil, water, or mixtures thereof.
35. The process of claim 11, wherein the marginal nonsolvent for PHA is a $C_3$—$C_{20}$ alcohol, $C_1$—$C_{20}$ alkane, fat, neutral lipid, oil, water, or mixtures thereof.

* * * * *